(12) United States Patent
Steding et al.

(10) Patent No.: US 6,727,375 B2
(45) Date of Patent: Apr. 27, 2004

(54) APPARATUS AND PROCESS FOR PREPARING SUBSTANTIALLY HALOGEN-FREE TRIALKOXYSILANES

(75) Inventors: Frank Steding, Marl (DE); Gerda Grund, Duelman (DE); Burkhard Standke, Loerrach (DE); Frank Kropfgans, Rheinfelden (DE); Michael Horn, Rheinfelden (DE); Albert-Johannes Frings, Rheinfelden (DE); Jaroslaw Monkiewicz, Rheinfelden (DE); Hans-Günther Srebny, Nienburg (DE); Claus-Dietrich Seiler, Rheinfelden (DE); Hans-Joachim Kötzsch, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/108,474

(22) Filed: Mar. 29, 2002

(65) Prior Publication Data

US 2002/0188146 A1 Dec. 12, 2002

(30) Foreign Application Priority Data

Mar. 30, 2001 (DE) .......................................... 101 16 007

(51) Int. Cl.$^7$ .................................................. C07F 7/04
(52) U.S. Cl. ..................................................... 556/470
(58) Field of Search ................................ 556/466, 470

(56) References Cited

U.S. PATENT DOCUMENTS

| | | | |
|---|---|---|---|
| 2,473,260 A | | 6/1949 | Rochow et al. |
| 3,641,077 A | | 2/1972 | Rochow |
| 4,727,173 A | | 2/1988 | Mendicino |
| 5,084,590 A | | 1/1992 | Ritscher et al. |
| 5,103,034 A | * | 4/1992 | Cho et al. .................... 556/470 |
| 5,177,234 A | * | 1/1993 | Nguyen et al. .............. 556/470 |
| 5,260,471 A | * | 11/1993 | Yamada et al. .............. 556/470 |
| 5,783,720 A | * | 7/1998 | Mendicino et al. .......... 556/470 |
| 6,090,965 A | * | 7/2000 | Lewis et al. ................. 556/470 |
| 6,380,414 B2 | * | 4/2002 | Brand .......................... 556/470 |

FOREIGN PATENT DOCUMENTS

| | | |
|---|---|---|
| DE | 2 247 872 | 4/1973 |
| DE | 100 33 964 | 1/2002 |
| EP | 0 280 517 B1 | 8/1988 |

OTHER PUBLICATIONS

CA:123:198304 abs of J Amer. Chem Soc by Gais et al 117(9) pp. 2453–66 1995.*
CA:123:83561 abs of Journal of Organic Chem. By Barnhart et al 60(14) pp. 4310–11 1995.*
CA:98:72316 abs of J of the Chem Soc, Chem. Comm. by Bertz et al (18) pp. 1030–2 1982.*
Hawley's Condensed Chemical Dictionary 12$^{th}$ edition editor RJ Lewis, Sr. 1993 publisher van Nostrand Reinhold, NY, NY.*
Chemical Abstracts, Database CA 'Online!, 1 page, XP–002248857, JP 11–269181, Oct. 5, 1999.

* cited by examiner

Primary Examiner—Jean F. Vollano
(74) Attorney, Agent, or Firm—Oblon, Spivak, McClelland, Maier & Neustadt, P.C.

(57) ABSTRACT

An apparatus for continuously preparing substantially halogen-free, in particular chlorine-free, trialkoxysilanes of the general formula I $$(RO)_3SiH \qquad (I)$$

in which R is an alkyl group having from 1 to 6 carbon atoms, has a main reactor unit (1), at least one metering unit (2, 3, 4) for liquids and/or suspensions, located upstream of the main reactor, and at least one metering unit (5) for gaseous and/or vaporous substances, and also a product workup unit (6) located downstream of the main reactor. A process for preparing substantially halogen-free trialkoxysilanes of the general formula I in which silicon is reacted with alcohols in an inert solvent utilizes at least one organocopper compound catalyst.

16 Claims, 2 Drawing Sheets

APPARATUS AND PROCESS FOR PREPARING SUBSTANTIALLY HALOGEN-FREE TRIALKOXYSILANES

BACKGROUND OF THE INVENTION

1. Field of the Invention

The invention relates to a process and apparatus for preparing trialkoxysilanes of the general formula I $$(RO)_3SiH \qquad (I)$$

in which R is an alkyl group having from 1 to 6 carbon atoms, by reacting silicon with alcohols in an inert solvent in the presence of a copper catalyst.

2. Discussion of the Background

It is known that monomeric hydroalkoxysilanes, such as trimethoxysilane or triethoxysilane, constitute a group of important key compounds in the organic chemistry of silicon.

Hydrosilylation by way of the Si—H function is a route to diverse functional organosilane compounds, examples being alkyl-, aminoalkyl-, haloalkyl-, vinyl-, and epoxyalkylalkoxysilanes. These compounds possess a very extensive field of application.

The monosilanes may be obtained in high purity by base-catalyzed dismutation of hydroalkoxysilanes. The monosilanes are used, for example, in the field of the semiconductor industry.

Hydroalkoxysilanes, such as triethoxysilane (TEOS) or trimethoxysilane (TMOS), are nowadays produced on the industrial scale by esterifying trichlorosilane with ethanol or methanol. Trichlorosilane is obtained in industrial volumes by reacting elemental silicon with hydrogen chloride. The process used in industry for producing TMOS and TEOS involves two stages, trichlorosilane synthesis and subsequent esterification. Because of the known high chemical aggressiveness of hydrogen chloride, both stages require a high level of plant investment and high ongoing costs for the servicing of such a plant. Moreover, the trichlorosilane synthesis yields chlorine-containing residues which are self-igniting and very awkward and expensive to dispose. TEOS or TMOS prepared by this process includes a significant chlorine content. The chlorine fraction in these products can be reduced into the ppm range only by means of very complex distillation processes.

Many fields of use are increasingly requiring the employment of chlorine-free organosilanes. Such silanes are unavailable by the customary preparation processes.

One approach to solving this problem might lie in the copper-catalyzed direct reaction of elemental silicon with alcohols, such as methanol or ethanol, to give TMOS or TEOS. The majority of the processes described, however, possess little technical relevance, despite the fact that the first patent applications in this area go back to as early as 1949 (U.S. Pat. No. 2,473,260). A particular disadvantage is the very low reactivity of the silicon grades used toward methanol or ethanol in a chlorine-free preparation technique, with the consequence that the yields obtained, based on the silicon used, are very low. Moreover, the preparation of the Cu/Si catalyst composition is highly complex, said composition being obtainable, for example, in accordance with the teaching of U.S. Pat. No. 3,641,077 by sintering of copper and silicon at 1050° C. followed by ultrafine grinding. Using methanol, after a reaction period of 4 to 5 hours at reaction temperatures of 280° C., only about 8% of the silicon used is converted to organosilanes—about 5% to TMOS and about 3% to tetramethoxysilane. Because of the lower reactivity of ethanol, only 6% of the silicon used is converted to organosilanes under otherwise identical reaction conditions—about 5% TEOS and about 1% tetraethoxysilane. Propanol and butanol are even less chemically reactive; the silicon conversions are 1.5% and 0.7%.

Of the direct dimethyldichlorosilane synthesis by means of a copper-catalyzed reaction of silicon with methyl chloride it is known that organosilanes are obtainable in high yields by the direct synthesis, by using chlorine agents. Apparently this is also the case for the direct synthesis of TEOS and TMOS. Industrially useful TEOS yields of more than 70%, with a selectivity of more than 90%, are described in DE-C 22 47 872. The catalyst used there is CuCl. Additional activation was achieved by using ethanol, with an addition of 0.17% HF. A chlorine-free product is, however, not obtained, owing to the use of CuCl as the catalyst. Moreover, the hydrogen fluoride admixed to the ethanol causes corrosion problems and also occurs in traces in the product.

Measures for further increasing the conversions are reported in European patent no. 0 280 517. There, the silicon powder used is activated beforehand using methyl chloride. The catalyst used is again CuCl. The TMOS conversion rates are stated as being 81% with respect to the silicon used, and the selectivity as being 88%. In the case of the synthesis of TEOS, the reactivity is much reduced: 60.2% silicon conversion with 78.4% selectivity. Again, the process does not operate without chlorine, and the yields are not very attractive for an industrial application.

U.S. Pat. No. 4,727,173 describes the chlorine-free preparation of trimethoxysilane with yields >80% (based on the silicon used) by reacting methanol with standard commercial silicon powder—purity: 98.5% by weight, Fe<0.5% by weight without further activation steps—under the influence of a copper(II) hydroxide catalyst. Subsequent experiments with standard commercial silicon powder, very finely ground, and $Cu(OH)_2$ catalyst in the synthesis of TMOS led only to unsatisfactory yields of approximately 30%. Furthermore, in comparison to the CuCl-catalyzed reaction an increased fraction of siloxanes was found—a consequence of the thermal decomposition of $Cu(OH)_2$ to CuO and water, which in turn hydrolyzes the trialkoxysilanes present, eliminating alkanol and forming siloxanes. In addition, a chlorine-free TEOS preparation with standard commercial $Cu(OH)_2$ as catalyst is generally not possible.

SUMMARY OF THE INVENTION

It is therefore an object of the invention to develop an economic process for preparing substantially chlorine-free trialkoxysilanes. This object is achieved in accordance with the invention as specified in the claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
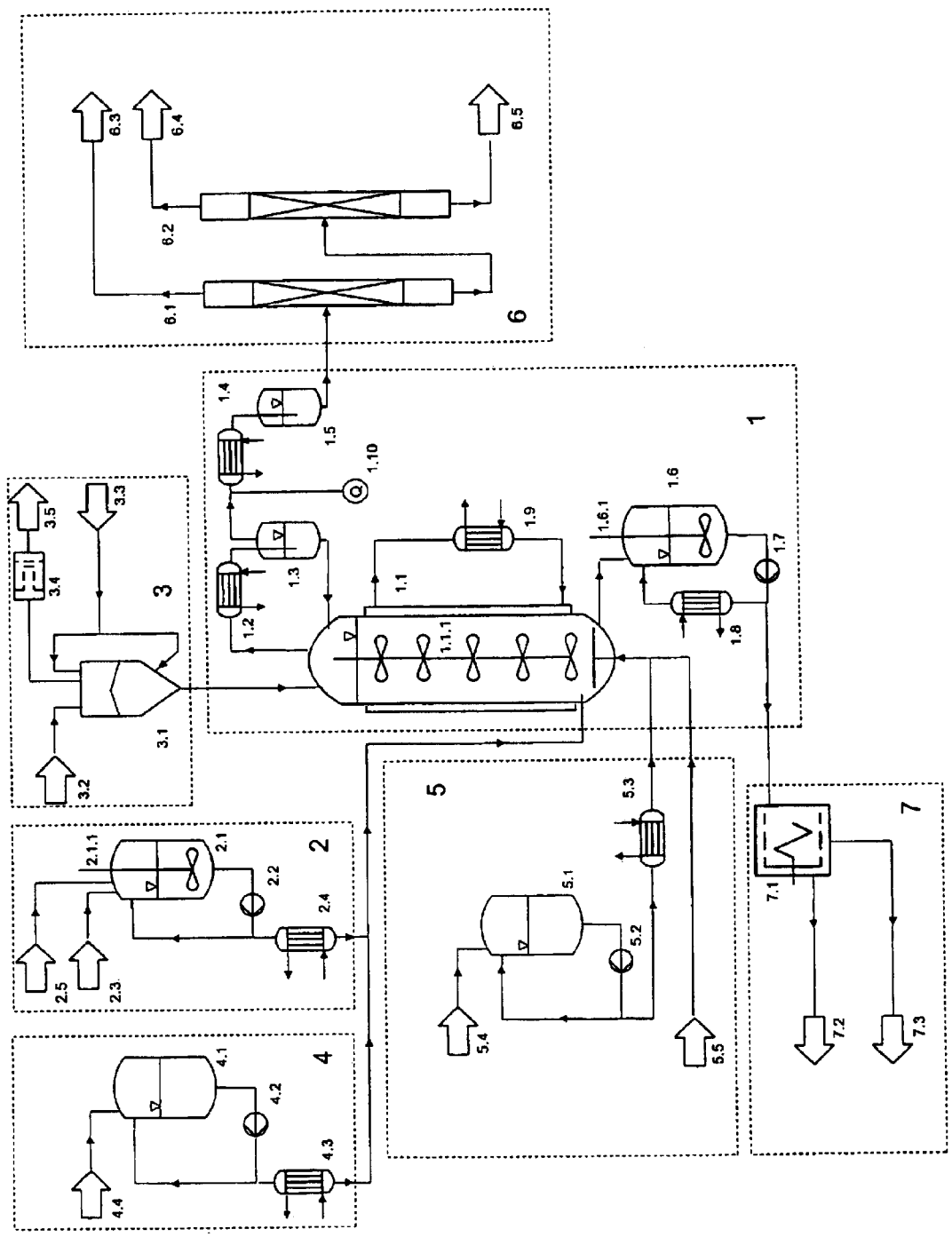
FIG. 1 shows the flow diagram of one preferred embodiment of the apparatus for continuously preparing substantially halogen-free trialkoxysilanes.

It has surprisingly been found that the reaction of silicon with alcohols in an inert solvent is best conducted in the presence of organocopper compounds as catalyst, giving particularly high yields and very good selectivities. The silicon used is appropriately in powder form, has been activated beforehand, and is low in iron. As the catalyst it is particularly preferred to use copper salts of neocarboxylic acids. It has also been found that the present process may be operated very economically as a continuous process.

The present invention accordingly provides a process for preparing substantially halogen-free, preferably substantially chlorine-free, trialkoxysilanes of the general formula I

$$(RO)_3SiH \qquad (I)$$

in which R is an alkyl group having from 1 to 6 carbon atoms, linear or branched alkyl groups being preferred, by reacting silicon with alcohols in an inert solvent in the presence of a copper catalyst, which comprises using at least one organocopper compound as catalyst.

By "substantially halogen-free", "chlorine-free" and, respectively, "substantially chlorine-free" trialkoxysilanes, the skilled worker generally understands those compounds whose halogen, halide, chlorine or chloride content, respectively, is within the region of the detection limit of the halogens, especially chlorine and/or chloride, i.e., a level of ≦5 ppm by weight.

The process of the invention for preparing trialkoxysilanes of the general formula I is generally a process in which not only gaseous and solid but also liquid components are involved under the prevailing reaction conditions.

The inert solvent is appropriately a hydrocarbon-based heat transfer oil, preferably a tritoluene isomer mixture, with particular preference MARLOTHERM® S. In the process of the invention the inert solvent serves generally as a reaction medium, in which the silicon used may be suspended.

In the process of the invention, the catalyst used comprises copper compounds which are preferably soluble in the inert solvent or in the alcohol used. The alcohol used is preferably ethanol or methanol. As compared with reactions conducted with heterogeneous catalysis, those reactions in which the catalyst is preferably present in the reaction medium in a dissolved form, i.e., generally in a homogeneously distributed form, afford distinct advantages. Substantially chlorine-free copper compounds soluble in a reaction medium could bring about particularly favorable reactivity in this way.

As the catalyst in the process of the invention it is preferred to use copper alkoxides or copper alkoxylates or copper carboxylates. Particularly preferred catalysts are copper carboxylates containing from 3 to 9 carbon atoms, with very particular preference being given to those having from 7 to 9 carbon atoms. Neocarboxylic acids in particular are used to prepare the copper carboxylates.

The copper carboxylates used as a preferred catalyst in the process of the invention are prepared, for example, from copper hydroxide and/or copper oxide, which originate from a substantially chlorine-free preparation process, and a carboxylic acid, with removal of the water of reaction. For this purpose, copper hydroxide and/or copper oxide is used, preferably with a superstoichiometric amount of carboxylic acid, in a molar ratio of 1:2, for example, and unreacted carboxylic acid may be removed by distillation together with the water of reaction. By way of example, the reaction may be conducted in a rotary evaporator. The water of reaction is removed preferably either by an azeotropic distillation or by means of vacuum distillation, appropriately in the temperature range between 20 and 180° C., preferably in the temperature range between 140 and 180° C. The maximum temperature is limited by the thermal stability of the copper alkoxylates or copper carboxylates and it will therefore generally be ≦280° C. The use of nitrogen for inert blanketing and lowering of the partial pressure is a further possibility.

The catalyst used in the process of the invention is preferably a copper carboxylate, including, for example, a solution thereof in ethanol—for example, a solution with a concentration of from 0.1 to 20% by weight, in particular from 2 to 5% by weight. Copper carboxylate prepared in this way may generally be described by the following stoichiometric composition:

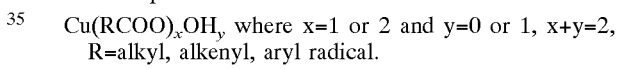

Cu(RCOO)$_x$OH$_y$, where x=1 or 2 and y=0 or 1, x+y=2, R=alkyl, alkenyl, aryl radical.

The copper carboxylates used as the preferred catalyst in the process of the invention may, however, also be prepared from metallic copper and a carboxylic acid. An excess of free carboxylic acid may be used. This reaction is preferably conducted at a temperature between 140 and 180° C. As a copper source it is, however, also possible to use the Si- and Cu-containing residue from the preparation of the trialkoxysilanes of the general formula I. After the copper has reacted with the carboxylic acid, insoluble constituents are generally filtered off and the filtrate is freed from excess acid by distillation, as already described above.

In the process of the invention it is preferred to use a pulverulent silicon which has been substantially freed from surface oxygen and silica and which with particular preference has a particle size $d_{90}$ of from 20 to 1000 μm and $d_{50}$ of from 10 to 800 μm, preferably $d_{50}$ of from 20 to 500 μm, with particular preference $d_{50}$ of from 30 to 200 μm, with very particular preference $d_{50}$ of from 10 to 100 μm. The particle size distribution (d values) was determined by means of laser scattering (Microtrac full range analyzer instrument type from Leeds and Northrup).

The silicon used here contains preferably less than 0.1% by weight iron. In the synthesis of TEOS by the process of the invention, for example, yields of more than 80% based on silicon used are possible, with the Fe content of the silicon used preferably not exceeding 0.03% by weight. By way of comparison, the yield of TEOS is around 50% where the Fe content of the silicon is in the region of 0.4% by weight. During the synthesis of trialkoxysilanes of the general formula I, operations should be carried out substantially free of iron, and contact of the reaction mixture with iron should be avoided. By way of example it is possible to use glass reactors, enameled reactors, copper reactors, copper plated reactors, and also instruments and apparatuses with comparable qualities and comparable surface properties, for the process of the invention.

The silicon used for the reaction in the process of the invention may be obtained by treatment with hydrogen fluoride, the solution used containing preferably from 0.1 to 40% by weight HF, with particular preference from 0.5 to 5% by weight HF. The silicon used is appropriately treated in an aqueous and/or alcoholic medium, preferably at a temperature of between 0 and 100° C., more preferably between 0 and 50° C., with particular preference between 10 and 40° C., and with very particular preference between 20 and 30° C.

Alternatively, the silicon used for the reaction may be pretreated in an aqueous and/or alcoholic medium having a pH>10. As a basic medium, use is made preferably of sodium hydroxide solution, with particular preference having an NaOH content of between 0.1 and 50% by weight, with very particular preference having an NaOH content of between 0.1 and 10% by weight.

The silicon powder is appropriately activated in a stirred apparatus with inert gas blanketing, e.g., nitrogen. The treatment time for activating the silicon is generally at least one minute, preferably from 5 minutes to 1 hour, with particular preference from 15 to 30 minutes. When using a solution containing NaOH, especially one with an NaOH concentration of more than 1% by weight, the silicon treatment time should not exceed a quarter of an hour.

Silicon thus treated may be separated from the aqueous and/or alcoholic phase under low-oxygen conditions, by filtration, for example, washed with water, preferably low-oxygen water, and/or alcohols, preferably methanol or ethanol, and subsequently handled likewise under low-oxygen conditions. By way of example, the residual fluorine content of silicon thus activated is around 50 ppm by weight down to the detection limit of fluorine. After washing, however, the treated silicon may also be dried, preferably in vacuo, with particular preference in vacuo at a temperature of between 0 and 180° C., in a rotary evaporator, for example. Alternatively, the activated silicon may be dried in other industrial drying apparatus, e.g., a paddle dryer, preferably under inertized conditions. After drying, the silicon powder is generally serviceable. The storage properties and handling of the extremely oxygen-sensitive powder may be improved and facilitated by suspending the activated silicon in, for example, MARLOTHERMS® immediately after treatment or after drying. The suspension may be used directly for the process of the invention for preparing trialkoxysilanes of the general formula I. As a general rule, the suspension is far less sensitive to oxygen than the dry activated powder. The use of such a suspension generally leads to no significant losses in activity even after about 1 hour of air contact. Nevertheless, until the reaction to give trialkoxysilanes of the general formula I, activated silicon is preferably handled under a low-oxygen inert liquid, with particular preference under the inert medium used for the reaction.

The reaction of silicon with alcohols in an inert solvent in the process of the invention in the presence of an organocopper compound catalyst is generally conducted in the temperature range between 100 and 350° C., preferably in the temperature range between 180 and 260° C., with particular preference in the temperature range between 200 and 250° C.

Additionally, the reaction of silicon with alcohols in the process of the invention in an inert solvent in the presence of an organocopper compound catalyst is preferably conducted at pressures of from 1 to 5 bar abs., with particular preference at pressures of between 1 and 3 bar abs.

When the reaction of silicon with alcohols is conducted in an inert solvent in the presence of an organocopper compound catalyst in the process of the invention, it is also possible to meter in the catalyst during the reaction. For this purpose, for example, the catalyst may be dissolved in the alcohol used in the reaction or in the inert solvent used as the reaction medium, and metered in as solution.

The inventive reaction of silicon with alcohols in an inert solvent in the presence of an organocopper compound catalyst is suitably also conducted in the presence of a defoamer, particularly in the presence of a methylsilicone oil, which preferably possesses a viscosity of between 0.65 to 1,000,000 mPa·s. Here, for example, it is possible to use dimethylpolysiloxanes having a molar weight of between 162 and 74,000 g/mol or corresponding mixtures as defoamers.

The process of the invention for preparing trialkoxysilanes of the general formula I, which comprises the reaction of silicon with alcohols in an inert solvent in the presence of an organocopper compound catalyst, may be conducted either batchwise or continuously.

Consequently, the present invention also provides apparatus for continuously preparing substantially halogen-free, preferably substantially chlorine-free, trialkoxysilanes of the general formula I

$$(RO)_3SiH \qquad (I)$$

in which R is an alkyl group having from 1 to 6 carbon atoms, preference being given to linear or branched alkyl groups, based on a main reactor unit (1), at least one metering unit (2, 3, 4) for liquids and/or suspensions, located upstream of the main reactor, and at least one metering unit (5) for gaseous and/or vaporous substances, and also a product workup unit (6) located downstream of the main reactor.

FIG. 1 shows the scheme of one preferred embodiment of the apparatus for continuously preparing substantially halogen-free, especially chlorine-free, trialkoxysilanes of the general formula I. The main reactor unit (1) comprises in general a heatable bubble column reactor (1.1) with multi-stage stirrer means (1.1.1) and jacket heating via the heat exchanger (1.9). Suitably mounted at the top of the bubble column reactor is a return flow condenser (1.2) which serves to separate the top product from the high boilers. The high boilers, such as the inert solvent, generally run back into the bubble column reactor as a liquid phase via vessel 1.3. The top product generally comprises the trialkoxysilane and excess alcohol, and small fractions of the solvent. Downstream of the means (1.2) there may be a further condensation means (1.4) and a collection vessel for top product (1.5).

Branching off from the bottom of the bubble column reactor (1.1) there is suitably a bottom product vessel (1.6) from which the further workup of the bottom product takes place, preferably the isolation of the discharged silicon from the solvent. The bottom product vessel (1.6) is generally equipped with stirring means (1.6.1). The bottom product may be circulated by the vessel (1.6) by means of a circulating pump (1.7) and a heat exchanger (1.8). The bottom product generally comprises only solvent in the liquid phase and unreacted silicon as a solid.

The reactants needed for carrying out the process of the invention may be supplied to the bubble column reactor by way of the metering units (2), (3), (4), and (5).

The metering unit (2) appropriately comprises an initial charge vessel (2.1) with substance feed (2.3), a stirrer means (2.1.1), an inert gas inlet (2.5), a circulation pump (2.2), and the facility to preheat the reactant flow via a heat exchanger (2.4). The metering unit (2) is used preferably for metering and supplying the catalyst solution into the main reactor unit (1).

The metering unit (4) preferably comprises an initial charge vessel (4.1) with substance feed (4.2), a circulation pump (4.2), and the facility to preheat the reactant stream via a heat exchanger (4.3). The metering unit (4) is used preferably for metering and supplying the solvent into the main reactor unit (1).

The metering unit (3) preferably comprises an initial charge vessel for solids (3.1) with a suitable substance feed (3.2), by pneumatic conveying, for example, an inert gas inlet (3.3), and a filter means (3.4) for solids separation. The metering unit (3) is used preferably for metering and supplying silicon powder into the main reactor unit (1).

The metering unit (5) preferably comprises means for metering gases (5.5), for nitrogen and gaseous reactants, for example, or a means of storing (5.1) and subsequently metering a liquid, such as methanol or ethanol, which may also be transferred, for example, to the gas phase or vapor phase by way of an evaporator (5.3), preferably in the form of a heat exchanger. The metering unit (5) is used preferably for metering and supplying alcohols into the main reactor unit (1).

Downstream of the main reactor unit (1) there is appropriately a product workup facility (6). This is composed generally of thermal separation processes for separating the components, e.g., a distillation column (6.1) for separating the unreacted alcohol from the trialkoxysilane, and the distillation column (6.2) for separating off relatively high-boiling components, substantially the solvent. Working up is preferably carried out by way of distillation columns with a low holdup. The use and combination of thin-film evaporators, falling-film evaporators, and distillation columns for gentle workup with short residence times is a further possibility.

Unreacted alcohol, from the product workup facility (6), for example, may be recycled to the process via the metering unit (5).

For process control in the process of the invention it is preferred to use an online hydrogen analyzer (1.10), e.g., an online thermal conductivity detector (TCD). This analyzer is preferably connected to the vapor line of the bubble column reactor, with particular preference upstream of the condenser (1.4). It is, however, likewise possible to integrate the hydrogen analyzer into the offgas line behind the product workup facility (6).

From the bottom product vessel (1.6), the bottom product preferably passes into a workup stage for solids separation, with particular preference a filter centrifuge or decanter. The unreacted silicon is discharged by way of the separation means (7.2) and may be passed on for further workup. The solvent and relatively high-boiling liquid components are discharged via the separation means (7.3) and may in part be recirculated via the metering means (4).

Unreacted alcohol, from the product workup facility (6), for example, may be recycled to the process via the metering unit (5).

The organocopper compounds soluble in the reaction medium of the process of the invention are generally of only limited stability over a prolonged period under the reaction conditions specified above. Despite this, the organocopper compounds used in the process of the invention bring about outstanding catalytic activity, very good selectivity, and high yields. Moreover, such copper catalysts have the advantage of being easy to add to the reaction mixture in liquid form, i.e., as a homogeneous solution, if catalyst activity subsides. Furthermore, the process of the invention may be conducted with particular economy in a continuously operated process. Trialkoxysilanes of the general formula I prepared by the process of the invention generally have residual chloride contents of only $\leq 3$ ppm by weight.

The present invention is illustrated by the following examples:

EXAMPLE 1

Batchwise Trialkoxysilane Synthesis Under Atmospheric Pressure

The laboratory apparatus described below was used:

A heatable 500 ml stirred glass reactor equipped with nitrogen blanketing, temperature measuring device, alcohol and catalyst metering device via a dipped pipe with metering pump, distillation device, consisting of a 20 cm glass column (packing: ceramic saddles), Dimroth condenser, and distillation receiver.

To carry out the reaction, the reactor is charged under nitrogen blanketing with 30 g of activated silicon, suspended in 250 g of MARLOTHERM® S, and solid catalyst, where appropriate, and this initial charge is heated to about 200 to 250° C. Subsequently, in a period of from 0.5 to 4 hours, first catalyst (about 1 g of Cu carboxylate in 30 g of alcohol) is supplied via the metering pump, followed by the alcohol (rate of addition: about 5 ml/min). If the reaction subsides, catalyst (1 g of Cu carboxylate in 30 g of alcohol) may be metered in further if desired at intervals of about 1 hour. The hydrogen evolved is determined volumetrically via a laboratory gas counter, as a measure of the silicon conversion. At regular intervals (approximately every 15 minutes) the product mixture leaving the reactor and condensed in the condenser is subjected to analysis by gas chromatography. The maximum trialkoxysilane concentration in the reactor condensate is determined. If the trialkoxysilane concentration in the reactor condensate falls below 1%, the reaction is terminated. The yield of trialkoxysilane is determined from the gravimetrically recorded total amount of reactor condensate, following determination of the composition by gas chromatography.

The duration of the reaction is between 4 and 6 hours. The conversions achievable are between 82 and 90% silicon, the selectivities for trialkoxysilane reach from 95 to 97%. The catalyst consumption is low, at an average of 3.5% Cu with respect to the silicon introduced.

The space/time yields in the batchwise experiments amount to approximately 1 mol/l h trialkoxysilane.

EXAMPLE 2
Batchwise Trialkoxysilane Synthesis Under Elevated Pressure

The glass apparatus described in Example 1 is replaced by a functionally equivalent, pressure tight apparatus. Suitable materials for the reactor include enameled steel, copper, or steel reactors with an inner copper lining.

The reaction regime corresponds to the mode of operating under atmospheric pressure. Installed behind the distillate receiver is a pressure regulator which maintains the desired system pressure.

The space/time yields are in the region of approximately 1 mol/l h at $p_{abs}$=1 bar, approximately 1.5 mol/l h at $p_{abs}$=2 bar, trialkoxysilane, with selectivities which remain virtually unchanged in comparison with the regime carried out under atmospheric pressure. At operating pressures of more than 5 bar abs., the selectivity for trialkoxysilane falls off.

EXAMPLE 3
Activation of Silicon

Ground silicon ($d_{V50}$=25 μm, $d_{V90}$=80 μm), approximately 1 kg, is suspended in 2 l of 1% by weight HF in a stirred reactor and treated at a temperature of between 20 and 30° C. for about 30 minutes. The contents of the reactor are subsequently run into a decanter or a filter centrifuge which can be rendered inert and can be heated, and are washed with about 2 to 3 l of ethanol. The residual alcohol moisture content may be adjusted to levels <5% by weight by heating the filter centrifuge or the decanter. The alcohol-moist or dry silicon powder treated in this way can be used directly for the reaction, but still retains the desired activity even after 10 days of storage under inert conditions.

EXAMPLE 4
Preparation of the Catalyst

The reaction for preparing the catalyst is conducted in a 1 l glass rotary evaporator. The apparatus may be evacuated by way of a connected water jet vacuum pump. It can also be rendered inert using nitrogen.

80 g of $Cu(OH)_2$, corresponding to 0.82 mol of Cu, and 302 g of neononanoic acid (CAS No. 59354-78-8), corresponding to 1.9 mol, are weighed into the flask. Under atmospheric pressure, the temperature is adjusted to about 160° C. for about 15 minutes. The water of reaction that goes over is condensed.

The pressure is then lowered to the achievable water pump vacuum, approximately 20 mbar, over the course of 10 minutes. The temperature is maintained at 160° C. for about 1 hour. Excess neononanoic acid is distilled off during this period.

Thereafter, the temperature is raised to about 180° C. and held for about 45 minutes in order to remove residues of neononanoic acid from the reaction mixture.

The apparatus is rendered inert with nitrogen and slowly cooled to about 70 to 80° C. At this temperature, about 600 g of ethanol are introduced into the flask of the rotary evaporator and mixed with the reaction product.

The apparatus is then cooled further. At about 30 to 40° C., the product is withdrawn. The catalyst prepared in this way is suitable for use.

$CuCl_2$ may be added to the catalyst described in accordance with the invention, as a Cu catalyst, in a Cu:Cl molar ratio 10:1, corresponding to an addition of 0.041 mol $CuCl_2$ for the above reaction mixture.

EXAMPLE 5
Batchwise Preparation of Triethoxysilane with Stored, HF-activated Silicon The reaction is carried out in a 2 l glass reactor with stirrer, top-mounted distillation column, filled with glass Raschig rings, and downstream condenser and distillate receiver. The alcohol is metered via a dip pipe using a metering pump. The catalyst solution is added either via an additional metering pump and a further dip pipe, or manually via an injector. The distillate is collected in fractionated form. In the gas offtake of the distillate receiver there is installed a gas meter as a volumetric gas counter.

Under a nitrogen atmosphere, 150 g of alcohol-moist Si powder with a residual moisture content of from 8 to 10% by weight are suspended in about 1300 g of MARLO-THERM® S. Then about 35 g of the catalyst are added to a 30% strength by weight solution of copper carboxylate, in this case copper neononanoate in ethanol, and about 30 g of silicone oil as antifoam are placed into the cold reactor.

Using a time program, the reactor is heated to about 240 to 250° C. During the heating procedure, the alcohol introduced with the silicon powder is distilled off. At about 180 to 200° C., a marked evolution of gas, $H_2$, occurs. The gas volume flow can be ascertained directly from the volumetric gas counter which is sited downstream of the distillate receiver. The course of the reaction may be monitored via the gas volume flow.

At a reactor temperature of about 200° C., ethanol is metered in. As a result of the ensuing exothermic reaction, the temperature rises rapidly to 250° C. The addition of ethanol is between 10 to 20 g/minute.

Because of deactivation of the catalyst, it is necessary in a subsiding reaction to meter in further catalysts at intervals of about 0.5 h, about 5 ml of the copper neononanoate/ethanol solution.

The distillate is collected in fractionated form and weighed. The product composition is determined by means of gas chromatography.

The total reaction duration is between 4 and 6 hours. The achievable conversions are between 82 to 90% of the silicon introduced, the selectivities for triethoxysilane are from 95 to 97%. The catalyst demand is low at 3.5% copper, based on the amount of silicon used. The space/time yield for triethoxysilane is on average about 1.4 mol/h l.

Figure 2:
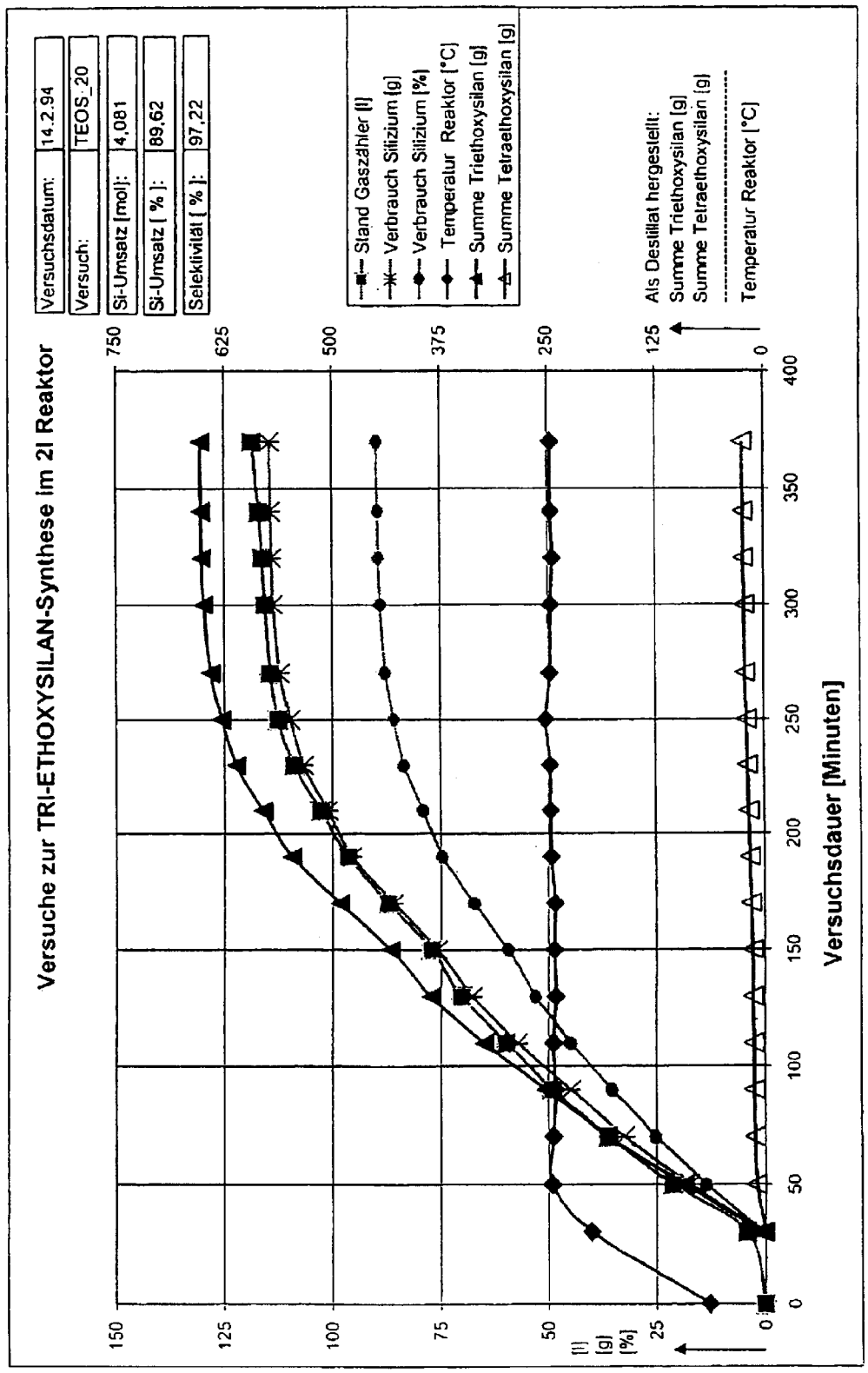
FIG. 2 is a graphical representation of the experimental results for Example 5.

Additionally, the experimental results for Example 5 are listed in Table 1 and depicted graphically in FIG. 2.

TABLE 1

Experimental results for Example 5

Experiment from preparing TEOS in a 2000 ml glass flask

| Reactant | | | | Mol. wt. | | | | end of experiment | | |
|---|---|---|---|---|---|---|---|---|---|---|
| Marlotherm ® AP ® 350 | 1270 g 30 g | | | TEOS Tetraethoxysilane Ethanol | 164.28 208.33 28.00 | | | Si residue Si conversion | 19.500 4.081 | [g] [mol] |
| Si powder Si moisture Catalyst*) | 150 g 15% 35 g | | | Ethanol | 46.07 | | | Si conversion Selectivity | 89.620 97.220 | [%] [%] |

| Experi-ment duration [min] | Fraction No. | Temp. in the reactor [°C] | Temp. at the top [°C] | S_gas level [l] | Fraction weight [g] | Ethanol mass [g] | GC analyses: ethanol [wt. %] | Triethoxysilane [wt. %] | Tetraethoxysilane [wt. %] | Ethanol [g] | Triethoxysilane [g] | Tetraethoxysilane [g] | Total triethoxysilane [g] | Total tetraethoxysilane [g] | Consumption silicon [g] | Consumption silicon [%] |
|---|---|---|---|---|---|---|---|---|---|---|---|---|---|---|---|---|
| 0 | 0 | 63 | 35 | 0.00 | | 0 | | | | | | | | | | |
| 30 | 1 | 199 | 135 | 4.15 | 145.6 | 122 | 95.59 | 2.21 | 0.17 | 139.18 | 3.21 | 0.24 | 3.21 | 0.24 | 0.58 | 0.46 |
| 50 | 2 | 245 | 150 | 21.30 | 259.7 | 365 | 55.29 | 34.49 | 3.65 | 143.60 | 89.57 | 9.47 | 92.79 | 9.71 | 17.12 | 13.43 |
| 70 | 3 | 244 | 151 | 35.90 | 267.0 | 609 | 61.40 | 32.71 | 0.53 | 163.92 | 87.34 | 1.41 | 180.13 | 11.12 | 32.20 | 25.25 |
| 90 | 4 | 242 | 151 | 49.00 | 256.5 | 857 | 667.96 | 28.38 | 0.29 | 174.31 | 72.78 | 0.73 | 252.91 | 11.85 | 44.70 | 35.06 |
| 110 | 5 | 244 | 151 | 59.85 | 266.5 | 1100 | 69.55 | 27.16 | 0.27 | 185.35 | 72.39 | 0.73 | 325.30 | 12.58 | 57.14 | 44.81 |
| 130 | 6 | 241 | 151 | 70.25 | 233.4 | 1348 | 70.27 | 26.25 | 0.34 | 164.00 | 61.27 | 0.80 | 386.57 | 13.38 | 67.68 | 53.09 |
| 150 | 7 | 243 | 148 | 77.30 | 286.0 | 1600 | 80.74 | 16.44 | 0.18 | 230.92 | 47.02 | 0.51 | 433.59 | 13.89 | 75.77 | 59.43 |
| 170 | 8 | 242 | 151 | 87.30 | 255.0 | 1845 | 73.19 | 22.83 | 0.44 | 186.64 | 58.21 | 1.11 | 491.79 | 15.00 | 85.84 | 67.32 |
| 190 | 9 | 246 | 156 | 96.50 | 253.5 | 2103 | 74.24 | 21.63 | 0.50 | 188.19 | 54.84 | 1.27 | 546.64 | 16.27 | 95.36 | 74.79 |
| 210 | 10 | 247 | 165 | 102.65 | 244.4 | 2332 | 83.16 | 13.25 | 0.36 | 203.24 | 32.39 | 0.87 | 579.03 | 17.14 | 100.99 | 79.21 |
| 230 | 11 | 247 | 164 | 108.80 | 258.2 | 2554 | 83.48 | 12.05 | 0.62 | 215.53 | 31.12 | 1.59 | 610.14 | 18.73 | 106.51 | 83.54 |
| 250 | 12 | 252 | 165 | 112.40 | 250.9 | 2800 | 89.11 | 6.90 | 0.37 | 223.58 | 17.30 | 0.92 | 627.45 | 19.65 | 109.58 | 85.95 |
| 270 | 13 | 247 | 165 | 114.20 | 263.5 | 3048 | 90.84 | 4.90 | 0.40 | 239.37 | 12.92 | 1.04 | 640.37 | 20.69 | 111.92 | 87.78 |
| 300 | 14 | 246 | 162 | 115.40 | 330.9 | 3396 | 93.70 | 2.42 | 0.29 | 310.04 | 8.01 | 0.96 | 648.38 | 21.65 | 113.42 | 88.96 |
| 320 | 15 | 244 | 158 | 116.00 | 291.4 | 3678 | 96.43 | 0.68 | 0.10 | 280.99 | 1.98 | 0.30 | 650.36 | 21.95 | 113.80 | 89.25 |
| 340 | 16 | 246 | 158 | 116.75 | 253.5 | 3886 | 95.86 | 0.39 | 0.26 | 243.01 | 1.00 | 0.66 | 651.35 | 22.61 | 114.06 | 89.46 |
| 370 | 17 | 246 | 155 | 118.30 | 375.0 | 4264 | 95.00 | 0.10 | 0.28 | 356.25 | 0.38 | 1.04 | 651.73 | 23.66 | 114.26 | 89.62 |

*)1 part by weight catalyst in 2 parts by weight ethanol

EXAMPLE 6

Continuous Trialkoxysilane Synthesis (Preparation of Triethoxysilane)

The experimental plant for continuous preparation of trialkoxysilanes of the general formula I essentially comprises the apparatus described in more detail above.

The activation of the silicon as in Example 3 takes place in a functionally equivalent pilot plant apparatus with a reactor volume of approximately 250 l. With the same proportions of the reactants, about 50 kg of silicon, 90 kg of 1% strength hydrochloric acid and 71 kg of ethanol are used.

The preparation of the catalyst as in Example 4 takes place in a functionally equivalent pilot plant apparatus with a reactor volume of about 35 l. With the same proportions of the reactants, about 6.8 kg of neononanoic acid, 1.8 kg of $Cu(OH)_2$ and 13.4 kg of ethanol are used.

The reaction is conducted in a 10 l steel bubble column with Cu jacket and Cu internals. The bubble column, which is equipped with a multistage stirrer, has an internal diameter of about 0.2 m and is fitted with a top-mounted column and a partial return flow condenser. The vapors are condensed and then passed to a rectifier. Alcohol is evaporated and passed via a gas distributor to the base of the bubble column. The gas distributor is configured as an annular nozzle with downwardly directed bores.

For starting up the reaction, activated silicon ($d_{V50}$ about 15 μm) and solvent are run as an approximately 20% suspension (starting batch) into the reactor. Catalyst, about 4% copper based on the amount of silicon, is added. In analogy to the batchwise operation, the reactor is heated to about 200° C. under a time program after which the metered addition of alcohol is commenced, about 120 mol/h. The alcohol is vaporized in a preheater and introduced via a gas distributor at the base of the bubble column. The temperature is raised to about 250° C., under atmospheric pressure. The course of the reaction is monitored continuously via the evolution of $H_2$, using an online thermal conductivity detector (TCD) in the offgas flow.

At about 200° C. there is marked evolution of $H_2$, which goes up as the temperature rises and reaches a plateau at a static reaction temperature. As soon as the evolution of $H_2$ drops, the starting batch has come to an end and HF-activated silicon can be added continuously at about 11 mol/h. At the same time, about 200 g/h of the 30% strength by weight Cu carboxylate solution are metered in as catalyst.

By means of this process it is possible, for example, in direct passage—i.e., without silicon recycling from the separation process—to achieve silicon conversions of about 65% and trialkoxy selectivity of about 98%. The space/time yield is approximately 0.85 to 1 mol/l trialkoxysilane.

Under steady-state operating conditions, the reaction may be operated with about 4 kg/h of ethanol and a molar metering ratio of 6.5 mol of ethanol based on 1 mol of silicon. The silicon solids content may fluctuate between 15 and 30%; it is preferred to establish a solids content of 20%. The catalyst metering is from 3 to 4 g of copper per 100 g of silicon. About 7.5 mol/h of triethoxysilane are obtained from the condensed distillate.

German application 101 160 07.0, filed on Mar. 30, 2001, is incorporated herein by reference.

Where ranges are provided, all values and sub-ranges between the stated values are included.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing halogen-free trialkoxysilanes, said process comprising reacting silicon with an alcohol having 1 to 6 carbon atoms in an inert solvent in the presence of a copper catalyst, wherein said copper catalyst comprises at least one copper alkoxide having 1 to 6 carbon atoms or copper carboxylate of the formula $Cu(RCCO)_xOH_y$, where x is 1 or 2, y is 0 or 1, x+y=2, wherein R is alkyl, alkyenyl or aryl, and said one or more halogen-free trialkoxysilanes are of formula I $$(RO)_3SiH \qquad (I)$$

where R is an alkyl group having from 1 to 6 carbon atoms.

2. The process as claimed in claim 1, wherein the at least one copper compound is soluble in the inert solvent or in the alcohol.

3. The process as claimed in claim 1, wherein the inert solvent is a tritoluene isomer mixture.

4. The process as claimed in claim 1, wherein the alcohol is ethanol or methanol.

5. The process as claimed in claim 1, wherein the copper catalyst comprises at least one copper alkoxide.

6. The process as claimed in claim 1, wherein the at least one copper carboxylate comprises a carboxylate radical containing from 3 to 9 carbon atoms.

7. The process as claimed in claim 6, wherein the at least one copper carboxylate is prepared by reaction of copper hydroxide and a carboxylic acid and water formed in said reaction is subsequently removed.

8. The process as claimed in claim 6, wherein the at least one copper carboxylate is prepared from metallic copper and a carboxylic acid.

9. The process as claimed in claim 1, wherein the silicon is a pulverulent silicon free from surface oxygen and silica.

10. The process as claimed in claim 9, wherein the silicon contains less than 0.1% by weight of iron.

11. The process as claimed in claim 9, wherein the silicon is pretreated with hydrogen fluoride.

12. The process as claimed in claim 9, wherein the silicon is pretreated in an aqueous and/or alcoholic medium having a pH>10.

13. The process as claimed in claim 1, wherein the reaction is conducted in a temperature range of between 100 and 350° C.

14. The process as claimed in claim 1, wherein the reaction is conducted at a pressure of from 1 to 5 bar abs.

15. The process as claimed in claim 1, wherein the reaction is conducted in the presence of a defoamer.

16. The process as claimed in claim 1, wherein the reaction is conducted continuously.

* * * * *